US00PP08828P

United States Patent [19]

Bloom

[11] Patent Number: Plant 8,828

[45] Date of Patent: Jul. 12, 1994

[54] ACHILLEA VARIETY CV. ANBLO

[75] Inventor: Alan H. V. Bloom, Diss, England

[73] Assignee: Blooms of Bressingham Ltd., Diss, England

[21] Appl. No.: 75,176

[22] Filed: Jun. 9, 1993

[51] Int. Cl.[5] ..... A01H 5/00

[52] U.S. Cl. ..... Plt./68.1

[58] Field of Search ..... Plt. 68.1

[56] References Cited

PUBLICATIONS

Huxley, et al, (Eds.) "*Achillea*", *The New Royal Horticultural Society Dictionary of Gardening* 1, The Stocton Press, N.Y., 1992, pp. 38–41.

*Primary Examiner*—James R. Feyrer

*Attorney, Agent, or Firm*—Synnestvedt & Lechner

[57] ABSTRACT

A new and distinct variety of Achillea plant called *Anblo* that is characterized by its dense, very hairy, light silver foliage, its pale yellow flowers, and tall, upright growth habit.

3 Drawing Sheets

BACKGROUND AND SUMMARY OF THE INVENTION

This invention relates to the discovery and asexual propagation of a new and distinct variety of Achillea (a member of the Compositae family that is commonly known as yarrow or milfoil). The new plant was discovered by Alan H. V. Bloom in July, 1979 growing in a cultivated planting of Achillea 'Moonshine' plants in a nursery in Bressingham, England. The new Achillea variety is believed to be a cross between A. 'Moonshine' and an unidentified Achillea variety—possibly *A. taygetea*—and has been named 'Anblo.' The new variety was first asexually propagated by Mr. Bloom in the same Bressingham nursery in 1981, and testing has shown that it maintains its distinguishing characteristics, as hereinafter set out, through successive asexual propagation using shoot cuttings.

The new Achillea 'Anblo' variety is a hardy, herbaceous perennial with a long flowering season. 'Anblo' may be distinguished from its parent, Achillea 'Moonshine,' and also from other Achillea plants that it most closely resembles, namely *Achillea taygetea*, by the following combination of characteristics:

The 'Anblo' variety grows taller and more upright than *A. taygetea*. 'Anblo' is more akin to 'Moonshine' in this respect, but is somewhat taller and more upright than 'Mooshine.' Mature plants of 'Anblo' do not produce the same woody growth as 'Moonshine,' yet are stronger stemmed than *A. taygetea*.

The Achillea 'Anblo' has dense silvery foliage which is lighter than other similar cultivars; the 'Anblo' hairs are a lighter silver than those of Achillea 'Moonshine.' The foliage of the 'Anblo' plant is also very hairy, more hairy than Achillea 'Moonshine.' In winter, mature plants of 'Anblo' carry little foliage (akin to taygetea) compared to the proliferation of foliage on 'Mooshine' from the previous season's growth.

The habit of Achillea 'Anblo' is of a medium growth rate, not as fast growing as 'Moonshine,' and it does not appear to be as invasive as the latter. The invasive roots that are produced, produce a mat of feathery leaves of silver grey-green color and stout upright stems carry wide flat flower heads.

The flowers are clustered tightly together as a rosette at base of the plant as the flowering stem develops, and as the flowering stem elongates upwards the flower clusters will open up. These clusters of individual flowers can clearly be seen when the stem is about half developed. Flowering will start June (at the earliest this could be May) through to September (at the latest this would be November). The earlier and later flowering stems will of course be shorter in height, probably as short as 30 cm.

The 'Anblo' flowers are a paler yellow than other similar varieties, including *A. taygetea*. Its flowers are much paler than those of 'Moonshine,' a pale primrose as opposed to the sulphur yeloow of 'Moonshine.' Furthermore, the 'Anblo' flower heads are about 25 percent bigger than those of *A. taygetea*.

'Anblo' is a cut and come again flower which, if dead-headed by the removal of dead flower stems or stems that have gone past their best, could flower three times during a season of from May to November. Thus, 'Anblo' is ideal for use in the production of cut flowers. 'Anblo' is also useful for garden decoration, and has potential as a dried flower as well.

BRIEF DESCRIPTION OF THE FIGURES

The accompanying drawings illustrate the new Achillea variety 'Anblo' in color as grown in Bressingham, England.

BOTANICAL DESCRIPTION OF THE PLANT

Figure 1:
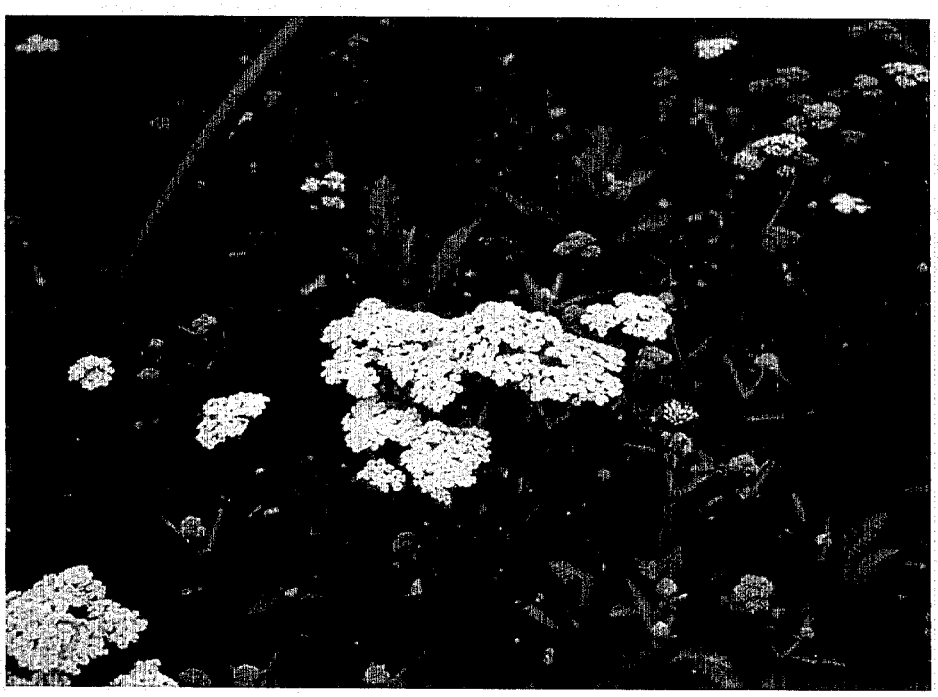
FIG. 1 is a photograph illustrating 'Anblo"s tall and upright growth habit, as well as its dense, silvery foliage.
Figure 2:
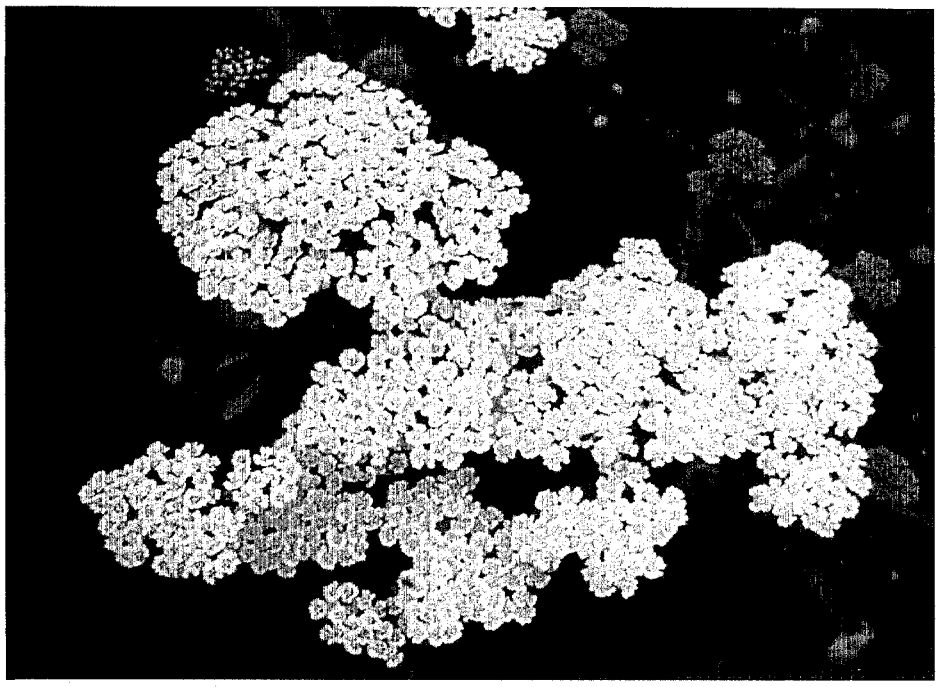
FIG. 2 illustrates 'Anblo"s pale yellow flowers, which are paler yellow than other similar varieties, including *Achillea taygetea* and Achillea 'Moonshine.' The drawing further demonstrates 'Anblo"s flower heads which are about 25 percent larger than those of Achillea taygetea.
Figure 3:
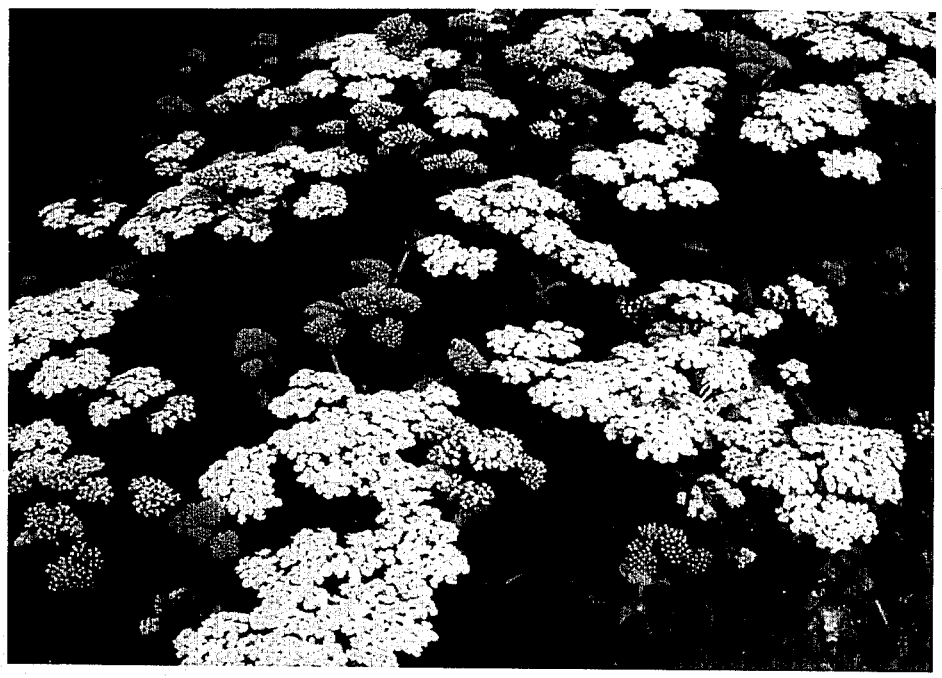
FIG. 3 is a photograph illustrating the new 'Anblo' variety at various stages of flowering. Here again illustrated is 'Anblo"s tall, upright growth habit and large, pale yellow flower heads.

Throughout this specification, color names beginning with a small letter signify that the name of the color, as used in common speech, is aptly descriptive. Color names beginning with a capital letter designate values basd on The R.H.S. Colour Chart published by The Royal Horticultural Society of London, England.

The descriptive matter which follows pertains to the 'Anblo' plants grown in Bressingham, England in July, 1989, and is believed to apply to plants of the variety grown under similar conditions of soil and climate elsewhere.

Name: Achillea cv. 'Anblo'.

Parentage: A cross of Achillea 'Moonshine' as the seed parent and an unidentified Achillea plant—possibly *A. taygetea*—as the pollen parent.

Size: Medium, about 30–70 cm in height; overall height at flowering is about 60–75 cm, with a spread of about 30 cm.

Growth habit: Medium and upright.

Strength: Hardy outdoors.

Root System: Fibrous.

Stems:

*Color before flowering.*—Silver grey/green.

*Color at flowering time.*—Silver grey/green.

*Type.*—Soild.

*Texture.*—Dull.

Foliage:

*Internodes.*—On flowering stems (length): 5.0 cm.

*Type.*—Herbaceous, most leaves dying back in winter.

*Arrangement.*—Large clump of basal leaves and small leaves on flower stem.

*Texture.*—Upper surface: very hairy, dull. Lower surface: very hairy, dull.

*Color.*—Upper surface: Greyed-Green. 191C, with silver hairs. Lower surface: Greyed-Green 191B, with silver hairs.

*Size.*—Length: up to 15 cm. width: up to 4 cm.

Average length×width: about 9×2 cm.

*Shape.*—Simple linear with parted leaf margins (feathery); 3 times, pinnate; lanceolate in outline.

*Petiole.*—About 3.5 cm in length.

*Margins.*—Dentate.

*Density.*—Medium.

*Fragrance.*—Astringent.

Inflorescence:

*Season.*—Mid-June to September.

*Duration.*—9 to 10 weeks, longer if dead-headed.

*Habit.*—Continuous.

Flowers:

*Size.*—Complete flower: 8–10 cm.

*Type.*—Single; dense terminal corymb.

*Habit.*—Carried well above basal foliage.

*Diameter.*—Capitulum: about 7 mm Umblelike clusters: about 10–12 cm.

*Borne.*—Solid array of numerous tiny flowers form umble-like clusters.

*Petals.*—Texture: smooth.

*Fragrance.*—Absent.

*Flower counts.*—Number of flowers per cluster: 25 to 45. Number of clusters: 4 to 6.

*Floret dimensions.*—Disc 1.49 mm. Ray 1.78 mm.

*Individual flower.*—Head diameter: 6.32 mm.

*Involucre.*—Calyx-like with one or more rows of bracts which very greatly in number, arrangment, form and consistency.

*Color.*—When petals first unfurl: Yellow 5C. When petals are half open: Yellow 4B. When petals are fully open: Yellow 4C fading to Yellow 4D. Ray Florets: Yellow 4B, fading later to Yellow 4C and Yellow 4D.

Table 1 provides a comparison of A. 'Anblo,' *A. taygetea* and A. 'Moonshine.'

TABLE I

Comparison Table of Achillea 'Anblo' with *A. taygetea* and A. 'Moonshine'

| | Height at Flowering | Spread | Internodal Length of Flowering Stem | Habit |
|---|---|---|---|---|
| 'Anblo' | 60–75 cm | 30 cm | 5.0 cm | More erect spreading habit Flowers primrose yellow fading to creamy yellow |
| *taygetea* | 50–60 cm | 45 cm | 3.5 cm | Mounded habit forming neat clumps. Flowers are sulfur yellow |
| 'Moonshine' | 60 cm | 45 cm | 4.0 cm | A Bressingham raised hybrid, mounded but spreading habit. The large flat heads are bright sulphur yellow. |

| | Flower Colour | | | |
|---|---|---|---|---|
| | First Open | Half Open | Fully Open | Fading to |
| 'Anblo' | RHS Yellow 5C | RHS Yellow 4B | RHS Yellow 4C | RHS Yellow 4D |
| *taygetea* | RHS Yellow 2A | RHS Yellow 2B | RHS Yellow 3B | RHS Yellow 3D |
| 'Moonshine' | RHS Yellow 7C | RHS Yellow 7A | RHS Yellow 7B | RHS Yellow 7D |

| | Foliage Colour | | Complete Flower Size |
|---|---|---|---|
| | Upper | Under | |
| 'Anblo' | RHS Greyed Green 191C | RHS Greyed Green 191B | 8–10 cm |
| *taygetea* | RHS Greyed Green 191B | RHS Greyed Green 191B | 6–8 cm |
| 'Moonshine' | RHS Greyed Green 191B | RHS Greyed Green 191C | 5–10 cm |

| | Dimensions of Florets | | Flower Counts | |
|---|---|---|---|---|
| | Disc | Ray | Number of Flowers per Clusters | Number of Clusters |
| 'Anblo' | 1.49 mm | 1.78 mm | 25 to 45 | 4 to 6 |
| *taygetea* | 1.13 mm | 1.58 mm | 9 to 20 | 4 to 6 |
| 'Moonshine' | 1.81 mm | 1.96 mm | 25 to 45 | 3 to 6 |

| | Foliage Size | | Diameter of Individual Flower Heads |
|---|---|---|---|
| | Length | Width | |
| 'Anblo' | To 15 cm | To 4 cm | 6.32 mm |
| *taygetea* | To 15 cm | To 4 cm | 4.27 mm |
| 'Moonshine' | To 20 cm | To 5 cm | 5.86 mm |

I claim:

1. A new and distinct variety of Achillea plant called Anblo as herein illustrated and described.

* * * * *

UNITED STATES PATENT AND TRADEMARK OFFICE

CERTIFICATE OF CORRECTION

PATENT NO. : PP 8828

DATED : July 12, 1994

INVENTOR(S) : Alan H. Bloom

It is certified that error appears in the above-indentified patent and that said Letters Patent is hereby corrected as shown below:

Column 2, line 12: "yeloow" should read --yellow--.

Column 3, line 64: "very" should read --vary--.

Column 4, line 3: Add the following sentence:
--Disc florets: Yellow 5C--.

Signed and Sealed this

Twenty-first Day of February, 1995

*Attest:*

*Attesting Officer*

Bruce Lehman

BRUCE LEHMAN

*Commissioner of Patents and Trademarks*